US012727875B2

(12) United States Patent
Cundiff et al.

(10) Patent No.: US 12,727,875 B2
(45) Date of Patent: Sep. 8, 2026

(54) SURGICAL SYSTEMS AND METHODS FOR TENDON REPAIR

(71) Applicant: Fusion Orthopedics USA, LLC, Mesa, AZ (US)

(72) Inventors: Adam J. Cundiff, Gilbert, AZ (US); Nathan G. Peterson, Gilbert, AZ (US); Eli W. Jacobson, Chandler, AZ (US)

(73) Assignee: Fusion Orthopedics USA, LLC, Mesa, AZ (US)

( * ) Notice: Subject to any disclaimer, the term of this patent is extended or adjusted under 35 U.S.C. 154(b) by 134 days.

(21) Appl. No.: 18/674,560

(22) Filed: May 24, 2024

(65) Prior Publication Data

US 2025/0359865 A1 Nov. 27, 2025

(51) Int. Cl.
*A61B 17/04* (2006.01)

(52) U.S. Cl.
CPC .. *A61B 17/0469* (2013.01); *A61B 2017/0404* (2013.01)

(58) Field of Classification Search
CPC .................... A61B 17/0469; A61B 2017/0404
See application file for complete search history.

(56) References Cited

U.S. PATENT DOCUMENTS 6,652,563 B2 11/2003 Dreyfuss
6,991,636 B2 1/2006 Rose
7,029,490 B2 4/2006 Grafton
7,077,845 B2 7/2006 Hacker
7,235,091 B2 6/2007 Thornes
7,892,256 B2 2/2011 Grafton
8,348,960 B2 1/2013 Michel
8,398,678 B2 3/2013 Baker
8,425,554 B2 4/2013 Denove
8,439,976 B2 5/2013 Albertorio
8,460,379 B2 6/2013 Albertorio
8,801,755 B2 8/2014 Dreyfuss
8,821,541 B2 9/2014 Dreyfuss
9,107,653 B2 8/2015 Sullivan
9,204,874 B2 12/2015 Denove
9,381,022 B2 7/2016 Bradley
9,526,493 B2 12/2016 Dreyfuss
9,549,726 B2 1/2017 Dreyfuss
9,855,029 B2 1/2018 Sullivan
10,143,469 B2 12/2018 Denove
10,206,694 B2 2/2019 Libby
10,258,320 B2 4/2019 Dreyfuss
10,820,899 B2 * 11/2020 George .............. A61B 17/0469
11,737,787 B1 * 8/2023 Chevalier .......... A61B 17/7216 606/258
12,458,338 B2 * 11/2025 Bachmaier ......... A61B 17/0401
2012/0161518 A1 6/2012 Schroeder et al.
2012/0203249 A1 8/2012 Schmidt
2018/0085110 A1 3/2018 Earhart
2020/0214851 A1 * 7/2020 Kalhorn ................ A61F 2/4611
2021/0338227 A1 * 11/2021 Federspiel ......... A61B 17/0401
2023/0218290 A1 * 7/2023 Earhart ............. A61B 17/0401 606/232

* cited by examiner

*Primary Examiner* — Katrina M Stransky

(57) ABSTRACT

Surgical systems and methods for performing a syndesmosis repair can comprise an inserter, a medial button, a locking button, and a suture. The inserter can comprise a rod including a dorsal member slidably coupled to a plantar member. The medial button end can be housed in a cavity in the rod until it is released. The medial button and the locking button are coupled using a knotless arrangement.

18 Claims, 11 Drawing Sheets

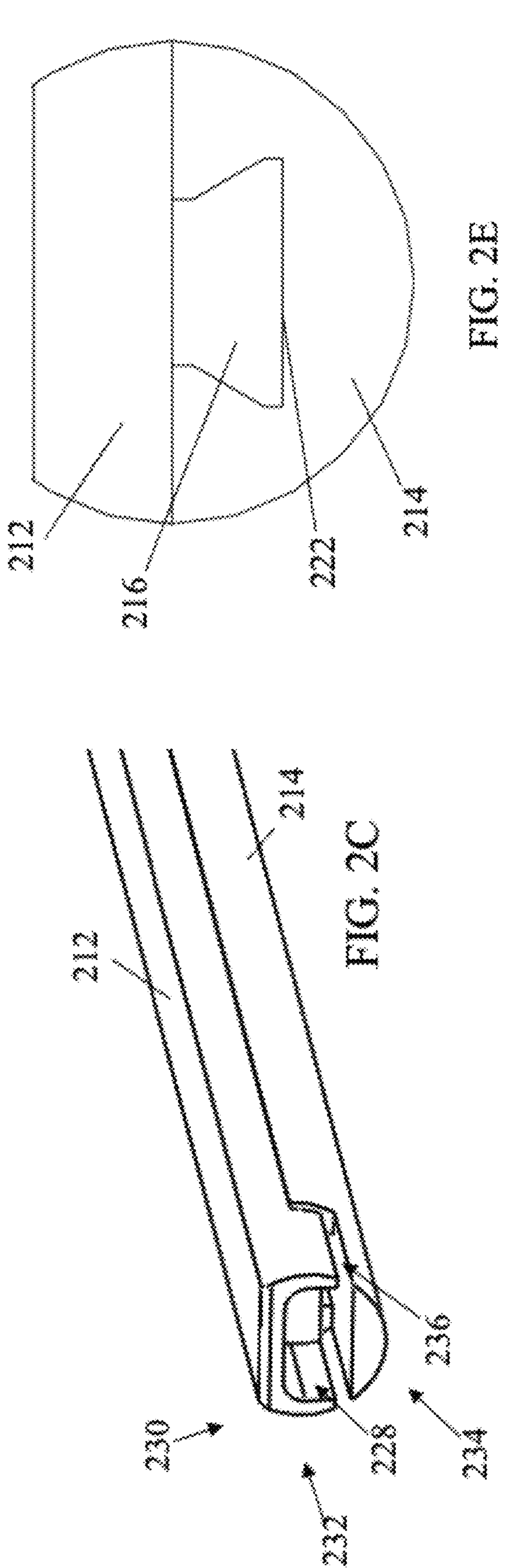
FIG. 2E
FIG. 2C
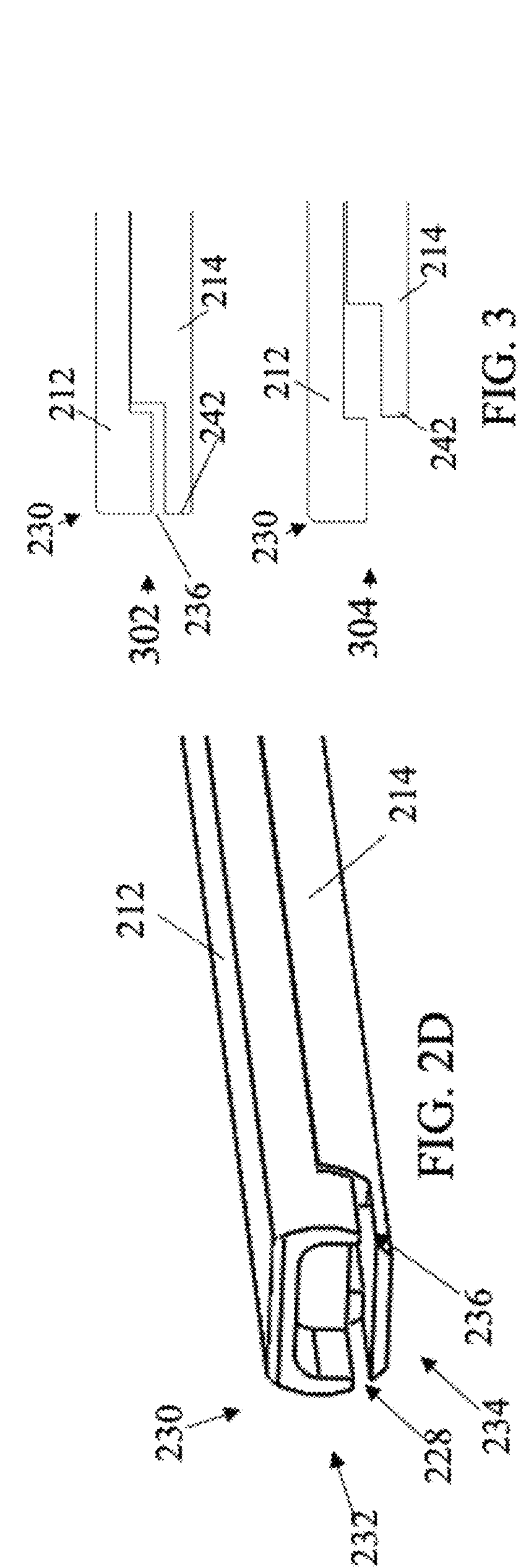
FIG. 3
FIG. 2D 906
210
800
904
902
236
908
912
600
914

910
500
600

D2

804

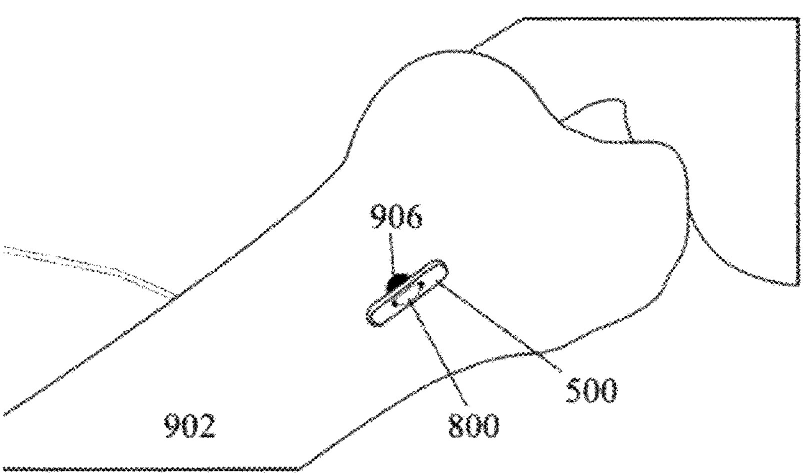
FIG. 9G
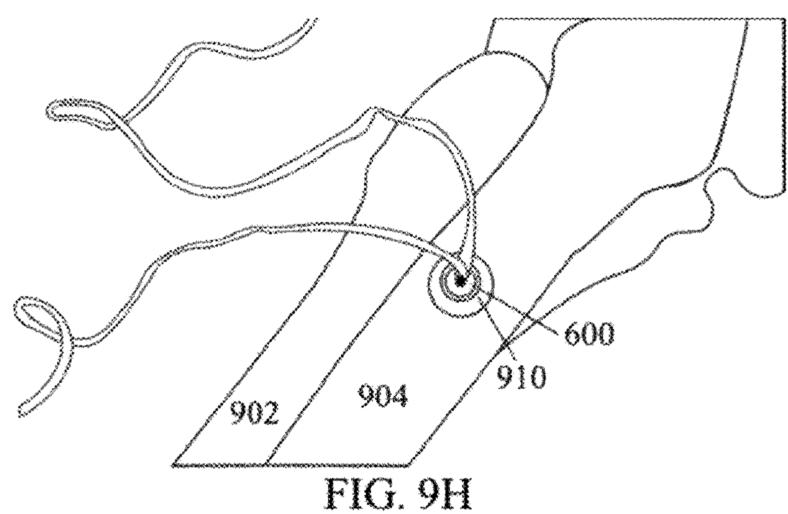
FIG. 9H
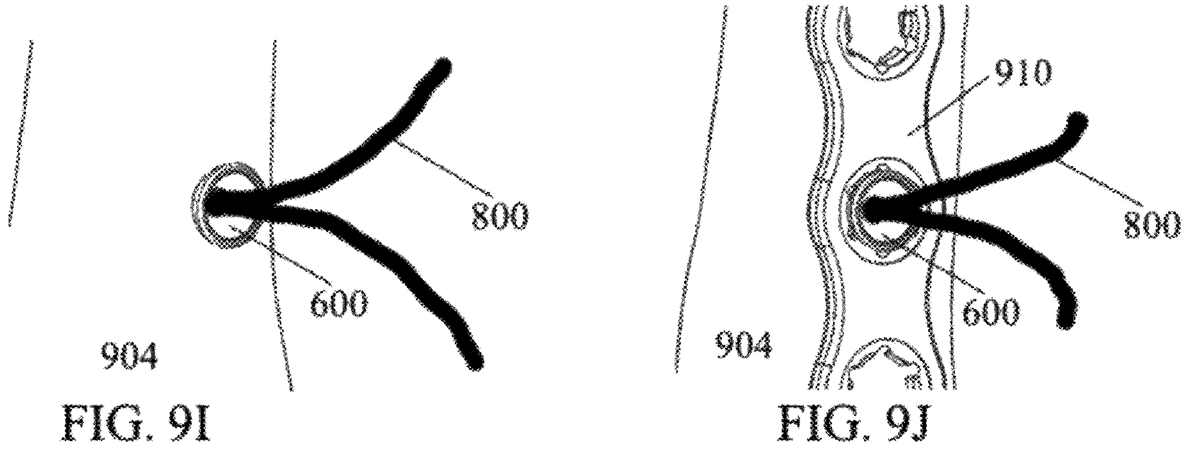
FIG. 9I
FIG. 9J

SURGICAL SYSTEMS AND METHODS FOR TENDON REPAIR

FIELD OF THE TECHNOLOGY

The present technology relates generally to orthopedic surgery, and more particularly to, surgical instruments and systems for performing a tendon repair.

BACKGROUND

Surgical intervention may be required for the repair of a tendon injury, specifically a syndesmosis injury. Each incision made increases the risk of infection. Fewer incisions assist with improved patient outcomes by improved healing time and avoiding possible infections. A method of performing a syndesmosis repair with fewer incisions is desired.

SUMMARY

A surgical system that can comprise an inserter. The inserter can be comprised of at least a rod. The rod can include a first end and a second end. The rod can be divided lengthwise from the first end to the second end into a first rod member and a second rod member. The first rod member can include at least a portion of the exterior surface of the rod. The second rod member can include at least a portion of the exterior surface of the rod. The second portion can be slidably coupled to the first portion and can be configured to slide between a first position and a second position. The first position can be a closed position. The second position can be an open position. The rod has a first end, and there can be a cavity formed in the first end of the rod. At least a portion of the walls defining the cavity can be part of the first rod member. At least a portion of the walls defining the cavity can be part of the second rod member. The first member and/or the second member can be flat along at least a portion of the length of the member to provide a "low profile" geometry to the rod.

The surgical system can comprise a handle. The surgical system can comprise a switch. At least a portion of the switch can be within the handle. The switch can be fixed to the second rod member. The surgical system can also comprise a safety pin that is removable from the handle and/or the switch. The safety pin can also be insertable into the handle and/or the switch.

The surgical system can comprise a medial button that includes at least two apertures. The surgical system can comprise a locking button including a face aperture, a first side aperture, and a second side aperture that define a pocket. The locking button can further comprise a suture slide which is a structure for preventing the suture from contacting other structures. The handle can comprise an aperture shaped to hold the locking button. The surgical system can further comprise a suture.

A method can comprise the steps of obtaining a suture, threading the suture through a medial button and a locking button, and obtaining a rod. The rod can include a first end and a second end. The rod can be divided lengthwise from the first end to the second end into a first rod member and a second rod member. The first rod member can include at least a portion of the exterior surface of the rod. The second rod member can include at least a portion of the exterior surface of the rod. The second portion can be slidably coupled to the first portion, and can be configured to slide between a first position and a second position. The first position can be a closed position. The second position can be an open position. The suture can comprise a first end and a second end. The medial button and the locking button can be a distance apart.

The method further comprising preparing at least one bone for tendon repair and placing the rod, at least a portion of the suture, and a medial button through the at least one bone. The method can further comprise shortening the distance between the medial button and the locking button.

BRIEF DESCRIPTION OF THE DRAWINGS

To readily understand the advantages and benefits of the technology, a more particular description of the technology briefly described above will be rendered by reference to specific embodiments that are illustrated in the appended drawings. Understanding that these drawings depict typical embodiments of the technology, and are therefore not to be considered to be limiting of its scope, the technology will be described and explained with additional specificity and detail through the use of the accompanying drawings, in which:

FIGS. 2A-2D is an isometric view of a diagram illustrating an embodiment of a surgical system including a rod;

FIG. 2E is a front view of a diagram illustrating an embodiment of a surgical system including a rod;

FIG. 3 is a side view of a diagram illustrating an embodiment of a surgical system including a rod with a first position and a second position;

FIG. 8 is an front view of a diagram illustrating an embodiment of a surgical system including a suture; and FIG. 9A-9J are drawings illustrating an embodiment of performing a syndesmosis repair with a surgical system.

DETAILED DESCRIPTION OF THE DRAWINGS

Figure 1:
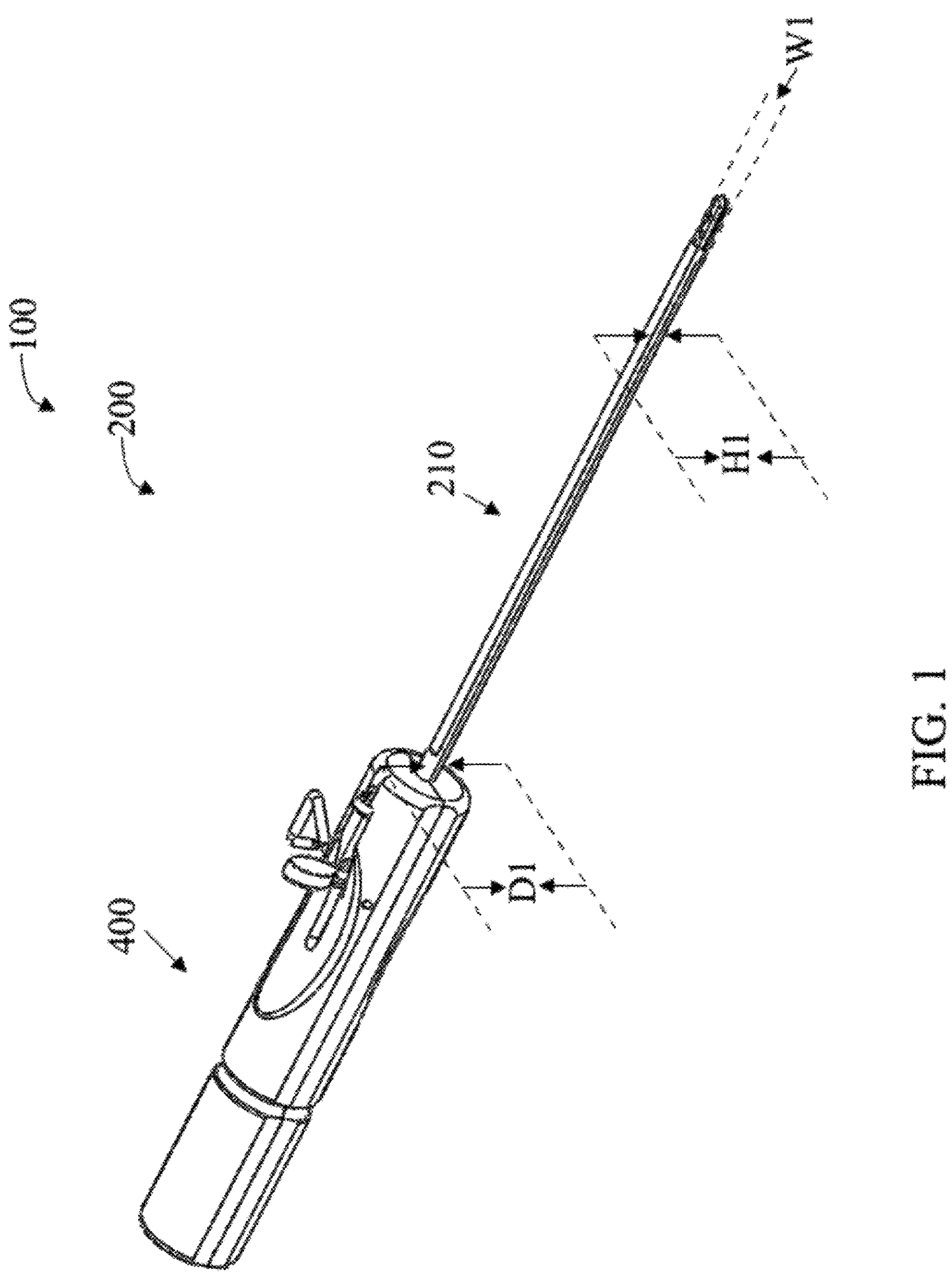
FIG. 1 is an isometric view of a diagram illustrating an embodiment of a surgical system including an inserter.

It should be understood that the language used in the present disclosure has been principally selected for readability and instructional purposes, and not to limit the scope of the subject matter disclosed herein in any manner. Further, reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including, but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments. Aspects of the embodiments are described below with reference to flowchart diagrams and/or block diagrams of methods, apparatuses, and systems according to embodiments. The flowchart diagrams and/or block diagrams in the Figures illustrate the structure, functionality, and operation of possible implementations of apparatuses, systems, and methods according to various embodiments.

It should also be noted that, in some alternative implementations, the functions noted in the block may occur out of the order noted in the Figures. For example, two blocks shown in succession may, in fact, be executed substantially concurrently, or the blocks may sometimes be executed in the reverse order. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment.

The present technology may include any type of surgical system and is not limited to the style of surgical system depicted in the drawings. Furthermore, the described features, structures, or characteristics of the various embodiments may be combined in any suitable manner. One skilled in the relevant art will recognize, however, that embodiments may be practiced without one or more of the specific details, or with other methods, components, materials, and so forth. In other instances, well-known structures, and/or materials are not shown or described in detail to avoid obscuring aspects of an embodiment.

Turning now to the Figures, FIGS. 1 through 9I are diagrams illustrating various views and/or embodiments of a surgical system 100. In various embodiments, the surgical system 100 can be utilized to perform a syndesmosis repair, bunion correction, Lis Franc procedure, distal bicep tendon repair, ACL reconstruction, and/or other procedures that are possible, each of which is contemplated herein.

The surgical system 100 may be constructed of any suitable material. In various embodiments, the surgical system 100 is constructed of a material that can be sterilized, and/or a material that is sterilized. In some embodiments, the surgical system 100 includes stainless steel, radio-opaque, titanium, titanium alloy, UHMW polyethylene, plastic, and/or aluminum, among other suitable materials that are possible, each of which is contemplated herein. In additional or alternative embodiments, the surgical system 100 includes surgical grade stainless steel, among other suitable surgical grade materials that are possible and contemplated herein. In some embodiments at least one portion of the system 100 can be sterilized.

Figures 2A, 2B:
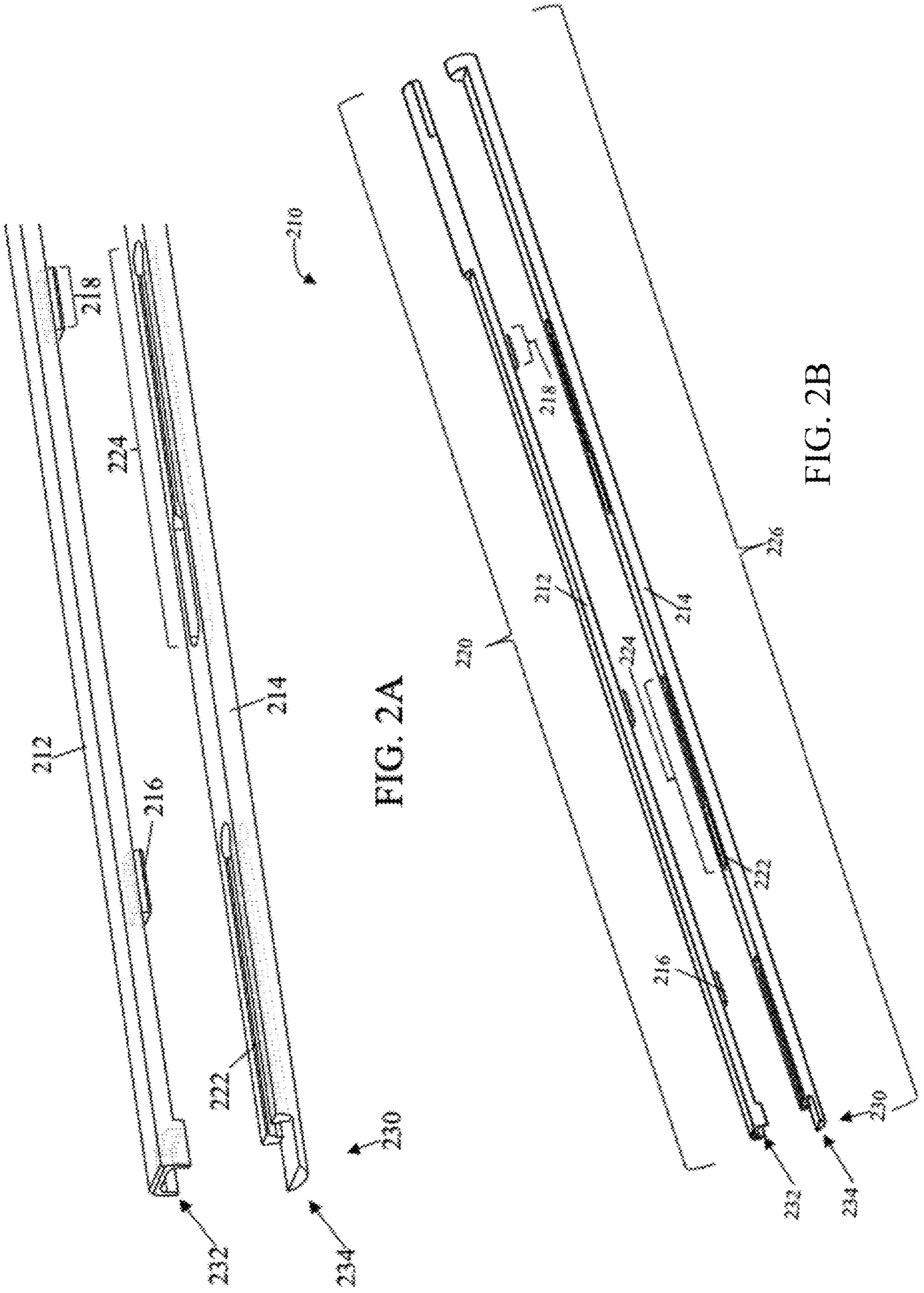
Figure 4A:
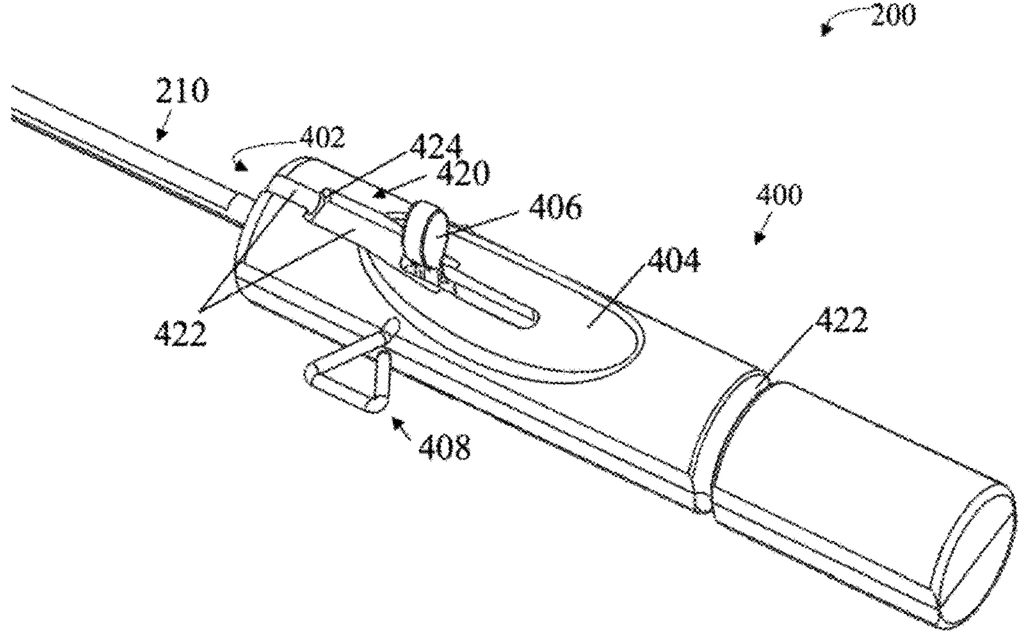
FIGS. 4A-4D are an isometric view of diagrams illustrating an embodiment of a surgical system including a handle.
Figure 4B:
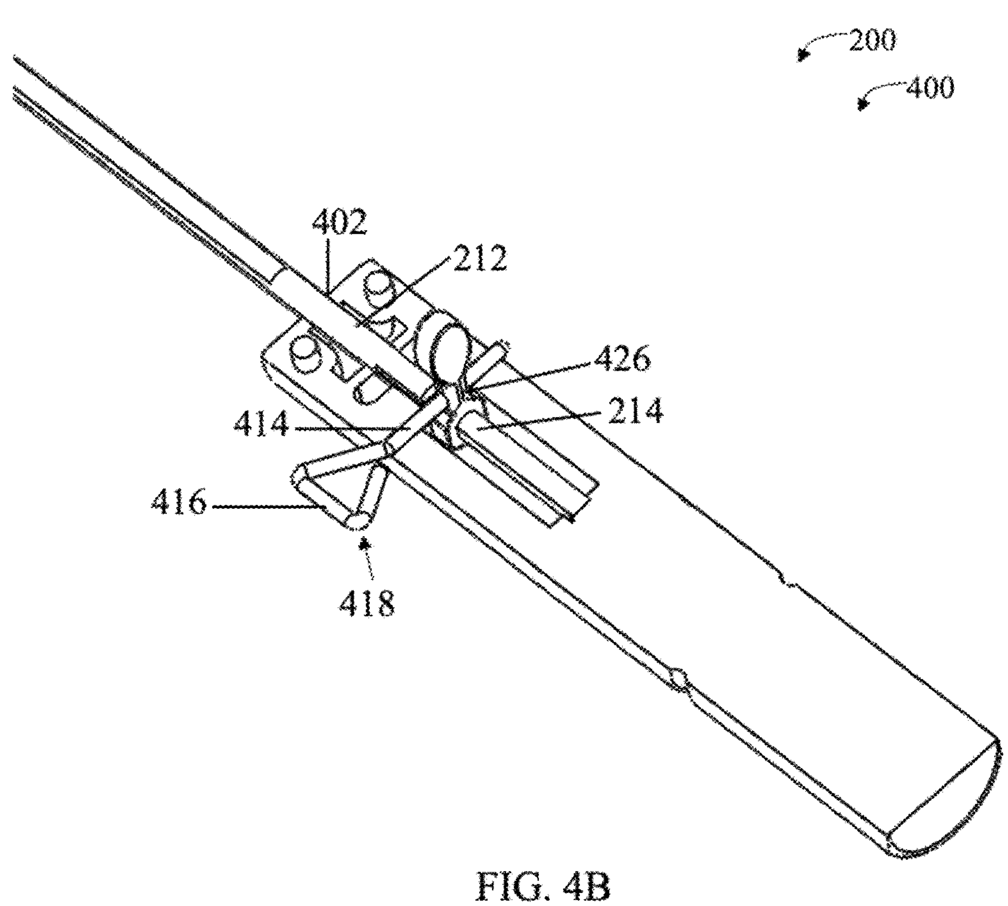
Figures 4C, 4D:
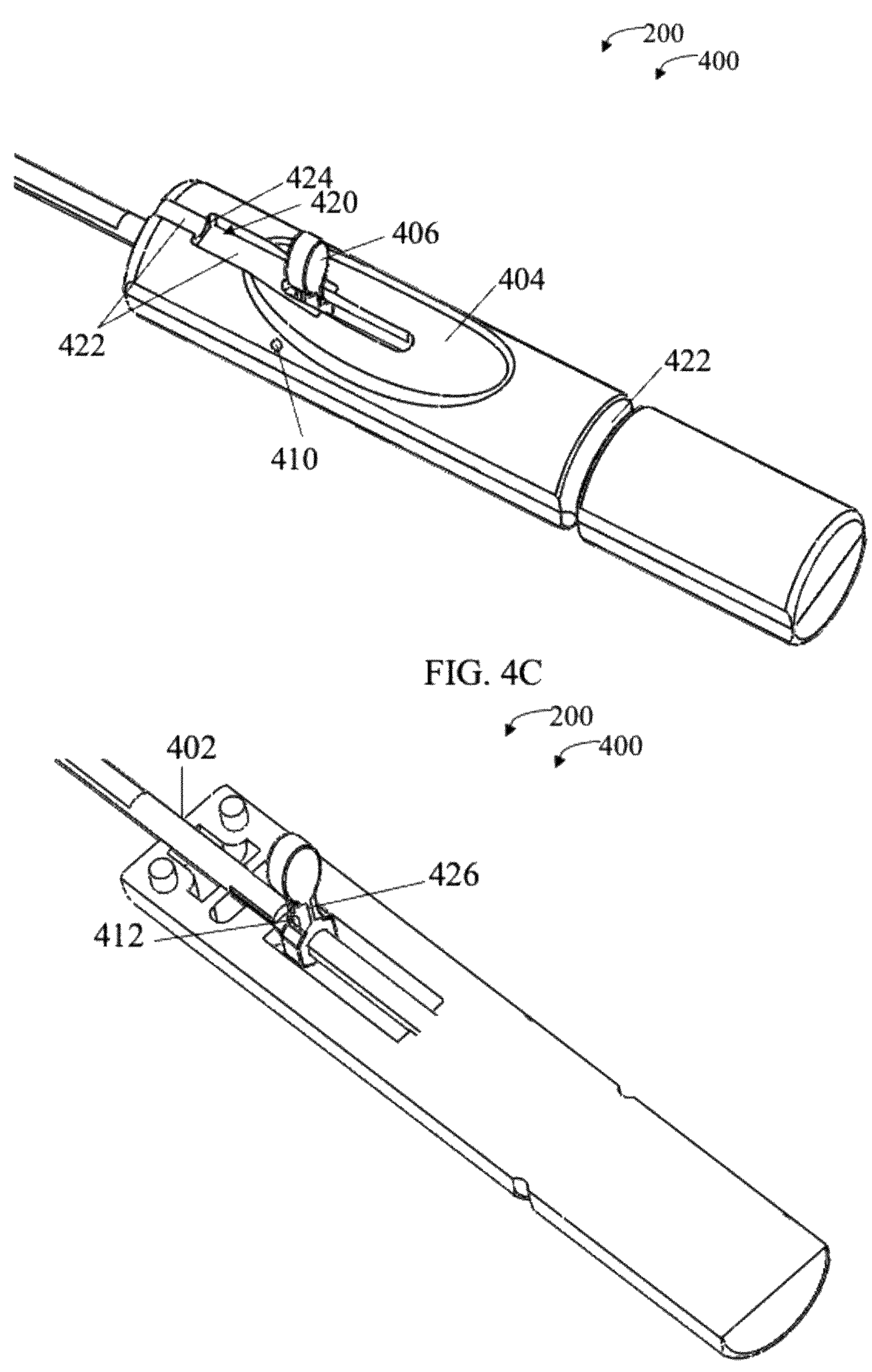

Referring now to FIGS. 1-2C. At least in the illustrated embodiment, the surgical system 100 includes, among other features, an inserter 200. At least in the illustrated embodiment, the inserter 200 includes a rod 210. In some embodiments the rod 210 can be a single piece. In some embodiments the rod 210 can include two or more pieces. In some embodiments, the rod can be split down the middle creating two approximately equal pieces (e.g., see FIG. 2A). In other embodiments the rod 210 can be split off center. The rod 210 can be split horizontally creating a dorsal member 212 and a plantar member 214 (e.g., see FIG. 2B), or the rod can be split vertically creating a medial member and a lateral member.

The following characteristics will be described in reference to either the dorsal member 212 or the plantar member 214 for illustrative purposes, but each characteristic could be employed on the dorsal member 212, the plantar member 214, the medial member, and/or the lateral member. In some embodiments the length 220 of the dorsal member 212 is the same as the length 226 of the plantar member 214. In other embodiment the dorsal member length 220 is different from the plantar member length 226.

The rod 210 can have a first cross-section that is circular, oblong, flattened, square, other shapes that are possible, each of which is contemplated herein. In some embodiments the rod 210 can include a second cross-section that can be circular, oblong, flattened, square, or other shapes that are possible, each of which is contemplated herein. In some embodiments the first cross-section can be circular, and the second cross-section can be flattened. For example, the rod 210 can have a circular first cross-section in some portions with a diameter D1, and a flattened ("low profile") second cross-section along other portions of the rod 210 such that a width W1 of the rod 210 is the same as D1, and a height H1 of the rod 210 is smaller than D1. In other embodiments the rod 210 can have a first circular cross-section in some portions with a diameter D1 and flattened ("low profile") second cross-section along other portions for the plantar member such that the width W1 is the same as D1 and the height H1 is smaller than D1. In some embodiments both the dorsal member 212 and the plantar member 214 are flattened ("low profile") (e.g., see FIG. 2D). In other embodiments the rod 210 can include more than two different cross-sections. In certain embodiments D1 can be in the range of two millimeters (2 mm) to five millimeters (5 mm). In some embodiments D1 can be 3.4 mm. In other embodiments D1 can be less than 3.4 mm. In further embodiments D1 can be greater than 3.4 mm.

Referring now to FIG. 2A-2E. The dorsal member 212 and the plantar member 214 can be slidably couplable. In some embodiments the dorsal member 212 is stationary (relative to the handle 400) and the plantar member is mobile. In other embodiments the plantar member is stationary (relative to the handle 400) and the dorsal member is mobile. In further embodiments both the dorsal member and the plantar member are mobile.

In some embodiments the dorsal member 212 can include at least one protrusion 216. The protrusion 216 can have a length 218. The protrusion length 218 can be the same length as the length 220 of the dorsal member 212, or the protrusion length 218 can be shorter than the dorsal member length 220. In some embodiments the plantar member 214 can include at least one groove 222. The length 224 of the groove 222 can be the same as the length 226 of the plantar member 214, or the groove length 224 can be shorter than and the plantar member length 226. The groove 222 can be shaped and sized to accept the protrusion 216. At least a portion of the groove 222 can be complimentary in shape to the protrusion 216 footprint. In some embodiments at least a portion of the groove 222 is shaped to prevent movement of the plantar member 214 in at least one direction for at least a portion of the groove (e.g. see, FIG. 2E). For example, in certain embodiments, the groove can prevent the plantar member 214 from separating from the dorsal member 212. In another example, the groove 222 can constrain the plantar member 214 to sliding between a first position and a second position. In some embodiments the groove 222 can constrain the plantar member 214 to sliding between at least two positions. In further embodiments the groove can constrain the plantar member 214 to sliding between more than two positions.

In certain embodiments the rod 210 can comprise a cavity 228 formed at a first end 230 of the rod. In the pictured embodiment the cavity 228 is formed through the surface of end 230 of rod 210. Portions 232 of the cavity 228 can be defined by the dorsal member 212, and portions 234 of the cavity 228 can be defined by the plantar member 214. The plantar cavity portion 234 can conform to the dorsal cavity portion 232, such that the cavity 228 has smooth connecting walls. In alternative embodiments the rod 210 can have a gap 236 between the dorsal cavity portion 232 and the plantar cavity portion 234.

Referring now to FIG. 3, the first end 242 of the plantar member 214 can be near the rod first end 230, creating a first closed position 302. The plantar member first end 242 can be some distance from the rod first end 230, creating a second open position 304. The plantar member 214 can slide relative to the dorsal member from the first closed position 302 to the second open position 304.

Referring now to FIGS. 4A-4D. The inserter 200 can include a handle 400. The handle can comprise plastic, aluminum, stainless steel, nylon, nitinol, titanium, and/or other materials that are possible, each of which is contemplated herein. In some embodiments the handle 400 can include a rod aperture 402 through which the rod 210 can couple to the handle 400. The handle 400 can also include at least one grip 404. The grip 404 can be at least one of a high friction surface, a shaped surface, a knurled surface, or other surfaces that are possible, each of which is contemplated herein. At least in the pictured embodiment the grip 404 can be a recessed portion of the handle 400 exterior surface. The handle 400 can include a locking button hole 420 which can be configured to hold the locking button 600 (described below) and can conform to the locking button 600. The locking button hole 420 can include a shoulder 424. The handle 400 can include at least one suture groove 422. The suture groove and/or grooves 422 are anything that can hold a suture to keep it generally within the profile of the handle, and/or to keep the suture in a specific position, for example at least one groove, hook, clip, tension plates, adhesive, or other devices that are possible, each of which is contemplated herein.

The inserter 200 can comprise a switch 406. The switch 406 can be fixedly coupled to the dorsal member 212. In some embodiments the switch 406 can be fixedly coupled to the dorsal member 212 and slidably coupled to the plantar member 214. In other embodiments the switch can be fixedly coupled to the plantar member 214 (e.g. see, FIG. 4B). In certain embodiments the switch 406 can be fixedly coupled to the plantar member 214 and slidably coupled to the dorsal member 212. The switch 406 can be a dial, knob, toggle, rod, switch, actuator, or other switching device(s) that are possible, each of which is contemplated herein. The switch can have a wrapping structure 426. The wrapping structure 426 can be any structure that is able to maintain tension on the suture. The wrapping structure 426 can be any structure that can increase tension on the suture as the switch is activated. The wrapping structure 426 can be at least one of a post, a neck, and/or a clip, among other possible structures, each of which is contemplated herein.

The inserter 200 can comprise a safety mechanism 408. The safety mechanism 408 can be any mechanism that maintains the first closed position 302. In some embodiments the safety mechanism 408 prevents movement of the plantar member 214 relative to the handle 400 and/or relative to the dorsal member 212. For example, the safety mechanism 408 can comprise at least one of a post, an aperture, a magnet, a tab, a switch, a screw, or other mechanisms that are possible, each of which is contemplated herein. In certain embodiments, the safety mechanism 408 includes a safety aperture 410 at least partially through the handle 400, a safety aperture 412 at least partially through the switch 406, and a safety pin 418 which can include a post 414, and a gripping portion 416.

Figure 5A:
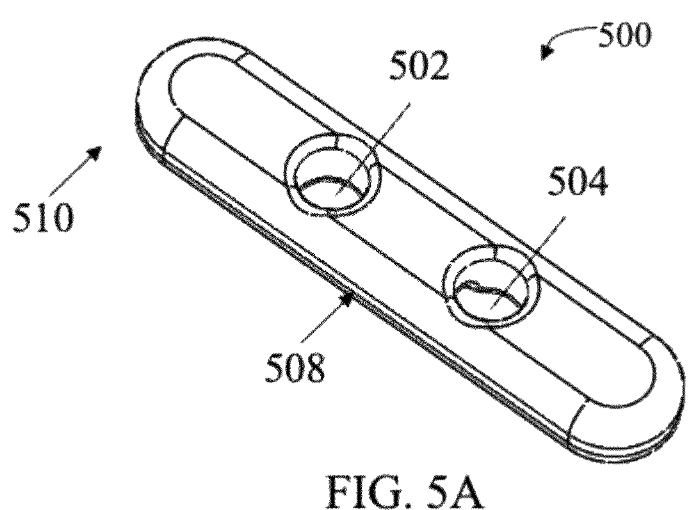
FIGS. 5A-5B are an isometric view of a diagram illustrating an embodiment of a surgical system including a medial button.
Figure 5B:
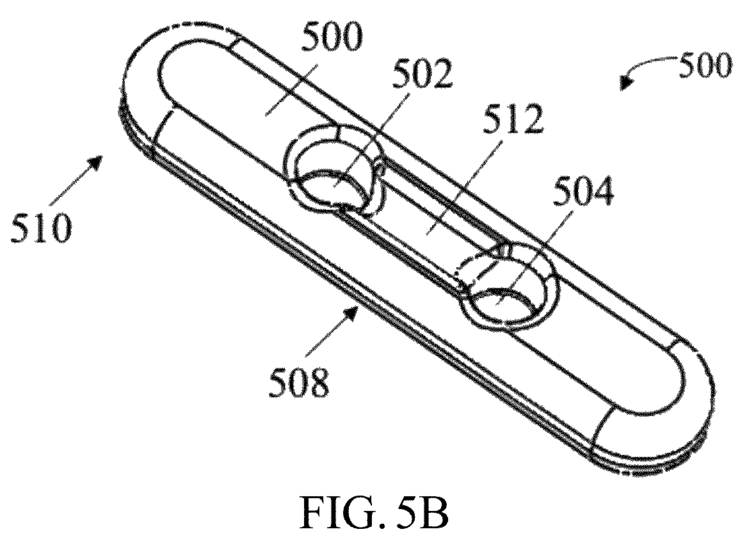
Figure 5C:
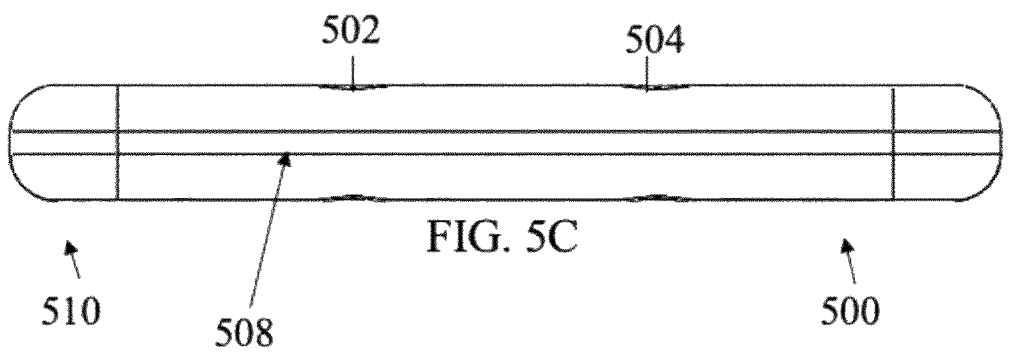
FIG. 5C is a side view of a diagram illustrating an embodiment of a surgical system including a medial button.
Figure 6A:
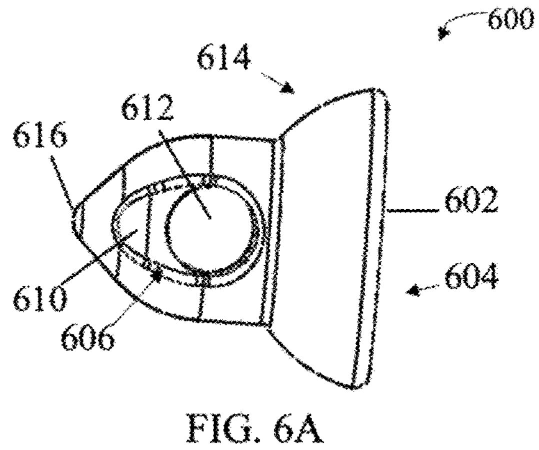
FIG. 6A is a side view of a diagram illustrating an embodiment of a surgical system including a locking button.
Figure 6B:
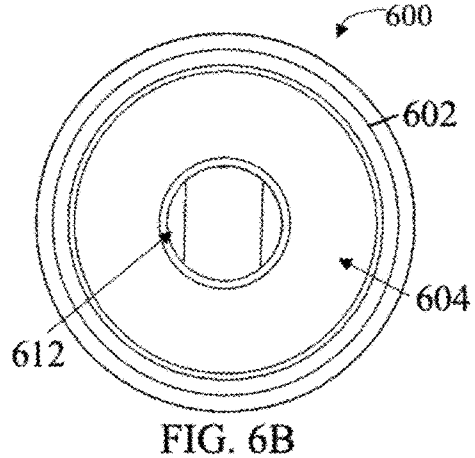
FIG. 6B is a front view of a diagram illustrating an embodiment of a surgical system including a locking button.
Figure 6C:
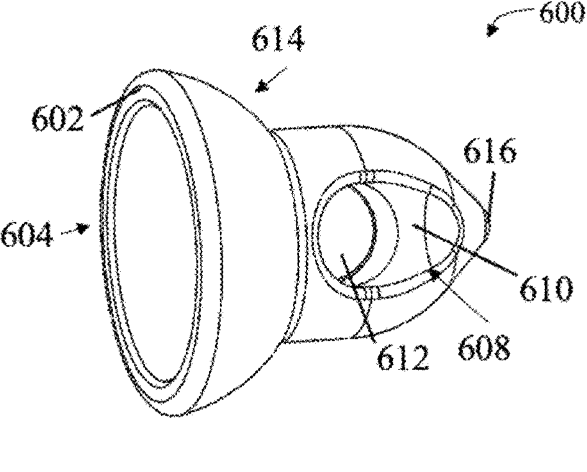
FIGS. 6C-6D are isometric views of a diagram illustrating an embodiment of a surgical system including a locking button.
Figure 6D:
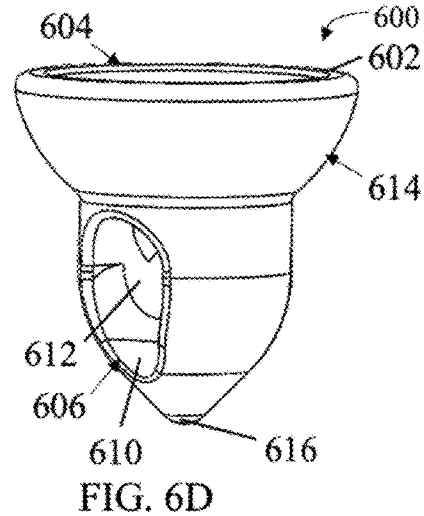
Figure 7:
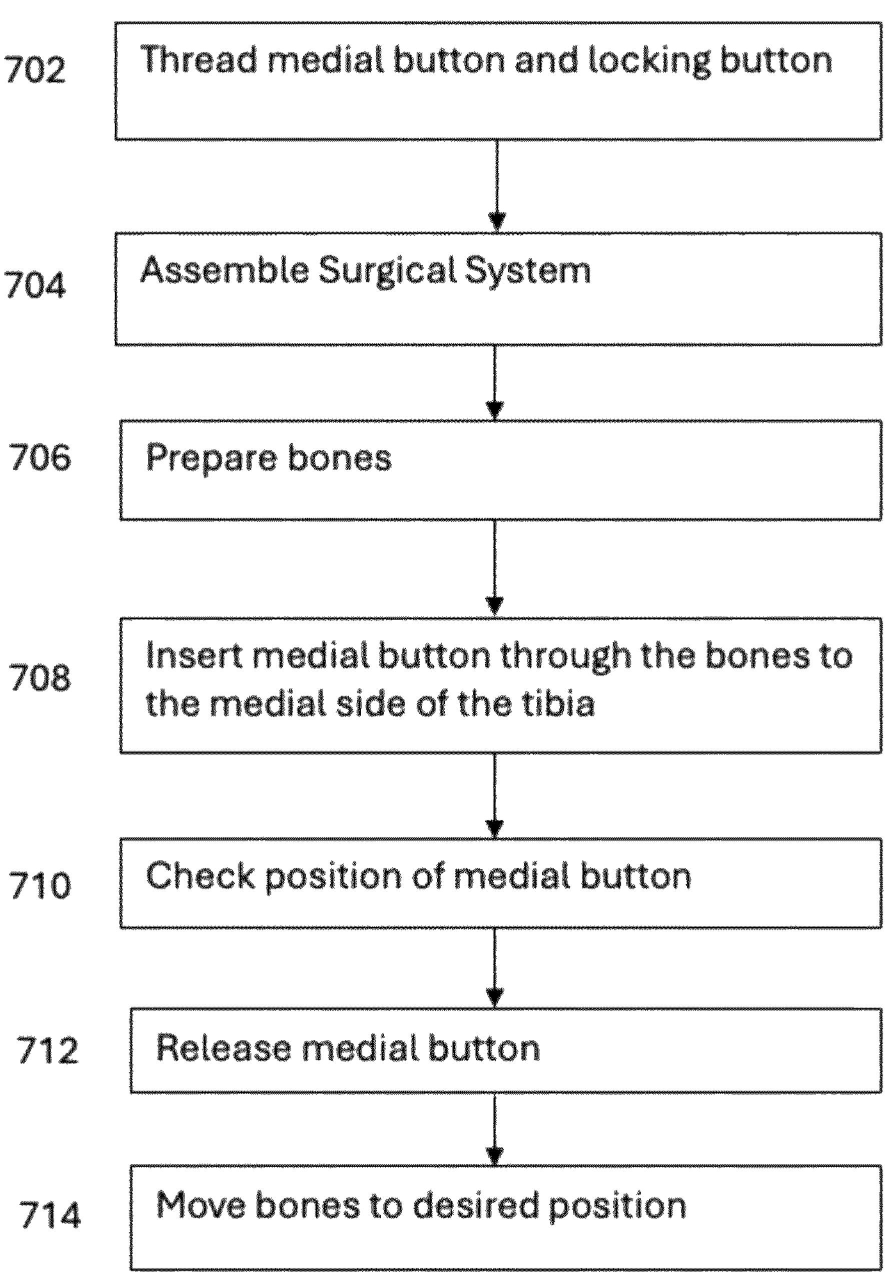
FIG. 7 is a flow chart illustrating an embodiment of performing a tendon repair with a surgical system.

Now referring to FIGS. 5A-5C. The surgical system 100 can comprise a medial button 500. The medial button 500 can be oblong, circular, rectangular, triangular, or other shapes that are possible, each of which is contemplated herein. In some embodiments the medial button 500 can comprise at least one aperture. In certain embodiments the medial button 500 can comprise a first aperture 502 and a second aperture 504. The medial button can include a canal 512 that extends across the first and second apertures 502 and 504. The medial button 500 can include at least one stabilizer 508 such as a groove, a protrusion, a magnet, a pressure fit, or other devices that are possible, each of which is contemplated herein. In at least one embodiment the stabilizer 508 includes a protrusion along the sides of the medial button configured to fit within gap 236. In other embodiments the stabilizer 508 is a pressure fit between the medial button end 510 and the cavity 228.

Now referring to FIGS. 6A-6D. The surgical system 100 can comprise a locking button 600. The locking button 600 can include a face 602 and a face aperture 604 through the face 602. The locking button 600 can have a first side that can include a first side aperture 606 and a second side that can include a second side aperture 608. The locking button first side and locking button second side can be different portions of one continuous and/or circular side of the locking button 600. The side apertures 606 and 608 and the face aperture 604 can define a pocket 612. The side apertures 606, 608 can include a suture slide 610. The suture slide 610 is any device, shape, surface, or mechanism that is configured to protect a suture from contact with other objects, such as at least one bone, washer, plate, hardware, and/or other objects that could exert friction to the suture and possibly causing the suture to tear over time, each of which is contemplated herein. In some embodiments the suture slide 610 can be a groove, one or more ball bearings, a shield, an eyelet, a grommet, or other devices and/or mechanisms that are possible, each of which is contemplated herein. In some embodiments the locking button 600 is shaped similar to a screw head. Specifically, an underface 614 can be tapered, straight, flat, or other screw head shapes that are possible, each of which is contemplated herein. The end 616 of locking button 600 can be tapered to assist in seating the locking button within a bone (e.g., a fibula), or a hardware 910 (described below).

Figures 8, 9A, 9B:
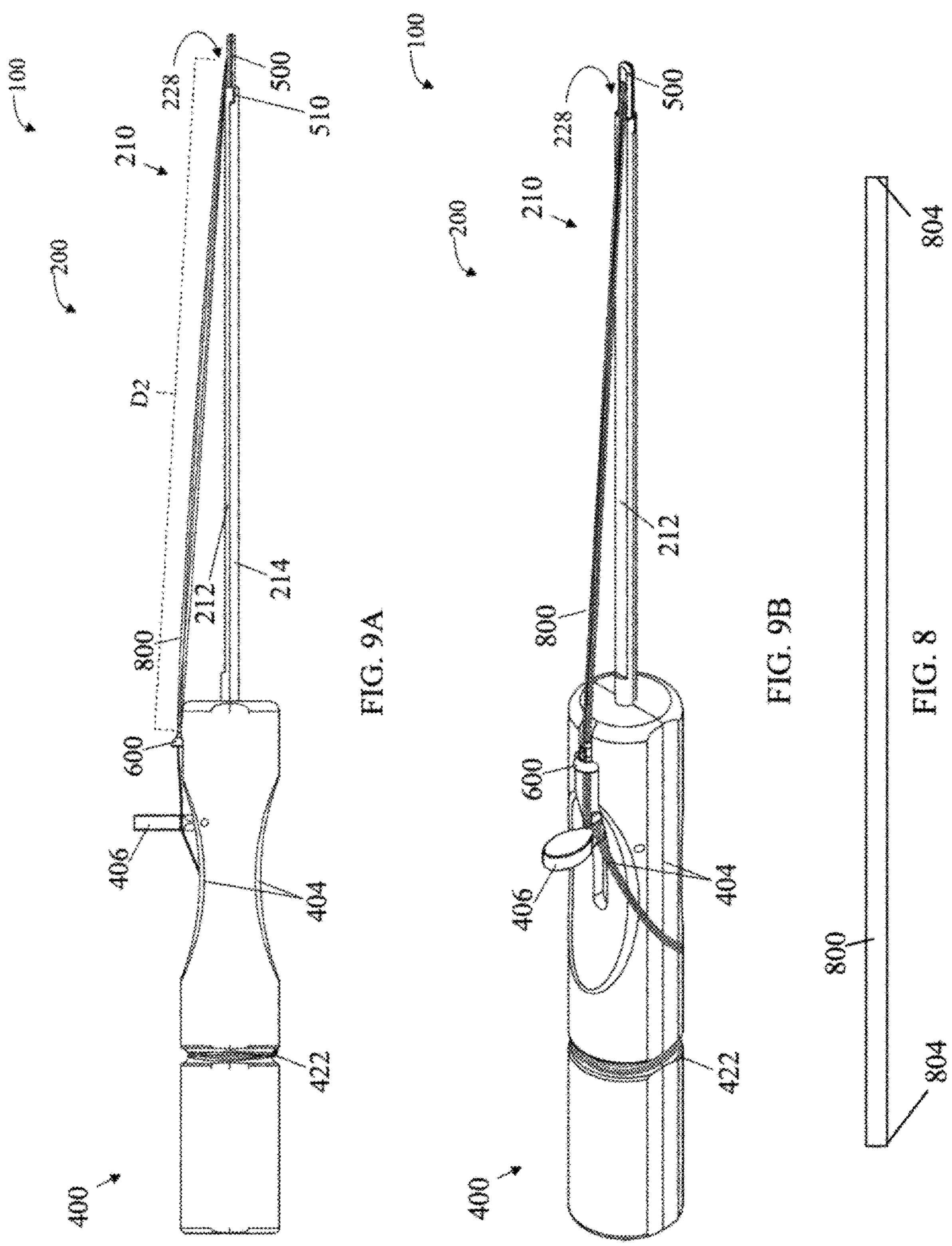
Figures 9C, 9D, 9E, 9F:
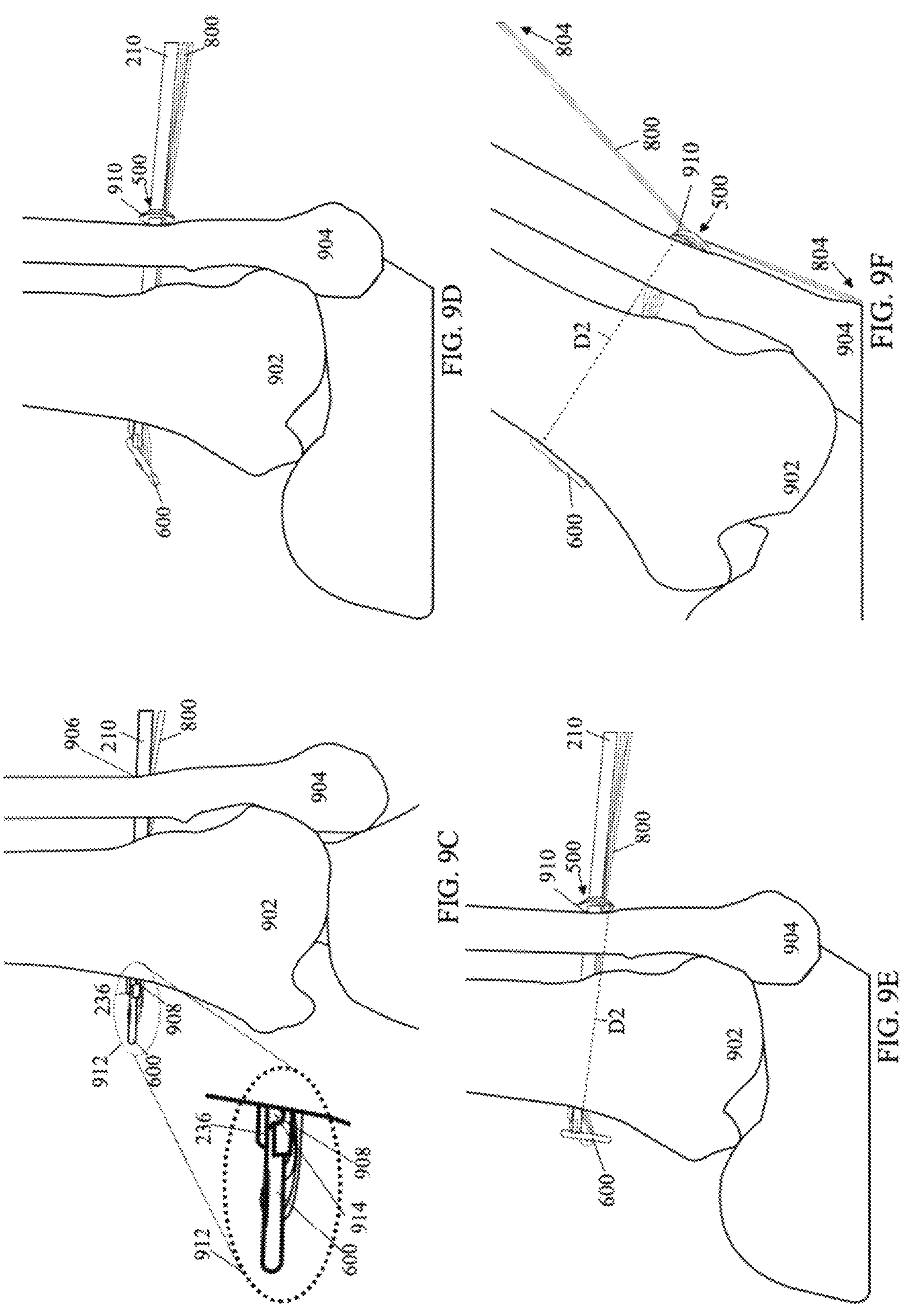

The surgical system 100 can include a suture 800 (e.g., see FIG. 8). The suture 800 can be anything that will maintain the desired distance D2 between the medial button 500 and the locking button 600 (e.g., see FIG. 9E), and can include at least one of a suture, a suture tape, a steel wire, and/or nitinol, among other materials that are possible, each of which is contemplated herein.

The use of the surgical system 100 will be described in reference to a syndesmosis repair. However, the surgical system 100 can be used in many other applications, such as tendon repair, bunion correction, Lis Franc procedure, distal bicep tendon repair, ACL reconstruction, or other surgical procedures that are possible, each of which is contemplated herein.

Referring now to FIGS. 7-9I, the medial button 500 and the locking button 600 can be threaded with a suture 800 (block 702). The buttons can be threaded together with a distance between the buttons D2. The suture 800 can be placed within the canal 512 of the medial button 500 so as to keep the profile as small as possible, and to protect the sutures 800 from contact with other objects and/or structures. At least a portion of the overlapping portions of the suture 800 (a "knot") can be contained within the pocket 612. The buttons 500 and 600 can be threaded to create a "knotless" configuration. The knotless configuration allows buttons to be moved closer together (shortening D2) by pulling the ends 804 of the suture 800, but does not allow the buttons to move farther apart (lengthening D2).

The surgical system can be assembled (block 704) the rod 210 can be placed in the first closed position 302 and the safety mechanism 408 can be engaged. The medial button end 510 can be placed within the cavity 228. The stabilizer 508 can be engaged. The locking button 600 can be placed in the locking button hole 420. The suture 800 can be wrapped around the switch wrapping structure 426 to maintain tension on the suture 800 and medial button 500. The suture 800 can be placed in the suture groove 422.

In at least one embodiment, a hole and/or holes 906 can be drilled through a tibia 902 and a fibula 904 (block 706). The inserter 200 can carry the medial button 500 through the hole(s) 906 (block 708) to a release position 912 where the medial button 500 has exited the hole(s) 906 completely (e.g., see FIG. 9C). The position of medial button 500 can be determined with the depth gauge 908 (block 710). The depth gauge 908 can be at least one of a space, a coating, a shape, a radiograph or other devices, each of which is contemplated herein. In some embodiments the depth gauge 908 is a space 914. The depth gauge 908 can be utilized by viewing the inserted rod 210 on a radiograph. When the release position 912 has been achieved, the space 914 can be visible medially of the tibia 904. The depth gauge 908 can eliminate the need for a medial incision which can reduce time for the procedure and risk of infection to the patient.

The switch 406 can be actuated (block 712), moving the plantar member 214 to the second open position 304 which allows the medial button 500 to move from an assembled position (assembled with the inserter) (e.g., FIG. 9C) over the first end 230 of the dorsal member 212 (e.g., see FIGS. 9D and 9E) to a discharged position. The inserter 200 can be removed. The medial button will be generally flush with the tibia medial side (e.g., see FIG. 9F). The two suture ends 804 can be pulled away from each other, shortening the distance D2 between the medial button 500 and the locking button 600, until the locking button is in desired position and the distance D2 between the buttons has reached its desired length (e.g., the tibia and fibula are the desired distance apart). At least a portion of the locking button underface 614 can be flush with the fibula (e.g., see FIG. 9I), or at least one hardware 910 (e.g., see FIGS. 9H and 9J). The hardware 910 can be a washer, a bone plate, a nail, a screw, or other devices that are possible, each of which is contemplated herein. The suture slide 610 can protect the suture 800 from contact with the hardware 910, preventing tearing or breakage of the suture 800.

The various embodiments discussed herein may be practiced in other specific forms and the described embodiments are to be considered in all respects only as illustrative, and not restrictive. The scope of the technology is, therefore, indicated by the appended claims rather than by the foregoing description. All changes that come within the meaning and range of equivalency of the claims are to be embraced within their scope. That is, one of ordinary skill in the art will appreciate that modifications and/or adaptations to the various aspects may be made without departing from the scope of the present technology, as set forth in the following claims.

What is claimed is:

1. A surgical apparatus comprising:
an inserter comprising:
a rod comprising a first end and a second end, wherein the rod is divided from the first end to the second end into a first rod member and a second rod member, wherein the first rod member includes at least a portion of an exterior surface of the rod, and the second rod member includes at least a portion of the exterior surface of the rod;
wherein at least a portion of the second rod member is slidably coupled to at least a portion of the first rod member and is configured to slide between at least a first position and a second position; and
a medial button including at least two apertures.

2. The surgical apparatus of claim 1, further comprising a cavity formed through the first end of the rod, wherein the first rod member comprises a first portion of the cavity and the second rod member comprises a second portion of the cavity.

3. The surgical apparatus of claim 2, wherein the cavity is closed when the second rod member is in the first position, and the cavity is open when the second rod member is in the second position.

4. The surgical apparatus of claim 1, wherein at least a portion of the first member is flattened.

5. The surgical apparatus of claim 1, further comprising a switch fixedly coupled to the second rod member.

6. The surgical apparatus of claim 5, further comprising a safety pin removably coupled to the switch to prevent movement of the switch in at least one direction when coupled to the switch and to allow movement of the switch in at least one direction when removed from the switch.

7. The surgical apparatus of claim 1, further comprising a handle comprising a body, wherein the handle is coupled to the rod.

8. The surgical apparatus of claim 1, further comprising a locking button wherein the locking button comprises a face aperture, a first side aperture, and a second side aperture, wherein the face aperture, the first side aperture, and the second side aperture define a pocket.

9. The surgical apparatus of claim 8, wherein the first side aperture includes a suture slide and the second side aperture includes a suture slide, wherein the suture slide inhibits a suture from contact with an intramedullary bone.

10. The surgical apparatus of claim 8, further comprising a handle comprising a body including an aperture configured to hold the locking button.

11. The surgical apparatus of claim 1, further comprising a suture.

12. A surgical system comprising:

an inserter comprising:

a rod comprising a first end and a second end, wherein the rod is divided from the first end to the second end into a first rod member and a second rod member, wherein the first rod member includes at least a portion of an exterior surface of the rod, and the second rod member includes at least a portion of the exterior surface of the rod;

wherein at least a portion of the second rod member is slidably coupled to at least a portion of the first rod member and is configured to slide between at least a first position and a second position;

a suture; and a medial button including at least two apertures, wherein the medial button is releasably couplable to the rod, and wherein at least a portion of the medial button is configured to be contained within the cavity.

13. The surgical system of claim 12, further comprising a cavity formed through the first end of the rod, wherein the first rod member comprises a first portion of the cavity and the second rod member comprises a second portion of the cavity.

14. The surgical system of claim 13, further comprising a switch fixedly coupled to the second rod member.

15. The surgical system of claim 14, further comprising a locking button wherein the locking button comprises a face aperture, a first side aperture, and a second side aperture, wherein the face aperture, the first side aperture, and the second side aperture define a pocket.

16. A method comprising the steps of:

obtaining a suture;

threading the suture through a medial button and a locking button;

obtaining a rod, wherein the rod comprises a first end and a second end, wherein the rod is divided from the first end to the second end into a first rod member and a second rod member, wherein the first rod member includes at least a portion of an exterior surface of the rod, and the second rod member includes at least a portion of the exterior surface of the rod;

wherein at least a portion of the second rod member is slidably coupled to at least a portion of the first rod member and is configured to slide between at least a first position and a second position.

17. The method of claim 16, further comprising:

preparing at least one bone to receive at least a portion of the suture;

placing the rod, at least a portion of the suture, and a medial button through the at least one bone.

18. The method of claim 17, wherein:

the suture comprises a suture first end and a suture second end;

the medial button and the locking button are a distance apart;

the method further comprising:

shortening the distance between the medial button and the locking button.

* * * * *